United States Patent [19]

Pearson et al.

[11] Patent Number: 5,302,171
[45] Date of Patent: Apr. 12, 1994

[54] BACK AND STOMACH SUPPORT DEVICE

[76] Inventors: David P. Pearson, 861 Bosthorn Ave., Newbury Park, Calif. 91320; Thomas J. Johnston, 24 Thunder Trail, Irvine, Calif. 92714

[21] Appl. No.: 851,598

[22] Filed: Mar. 16, 1992

[51] Int. Cl.$^5$ ............................. A61F 5/00; A61F 5/37
[52] U.S. Cl. ............................................ 602/19; 128/876
[58] Field of Search ............... 602/19; 2/338, 339, 2/312; 128/876; 272/123, 143; 273/DIG. 11, 30, 189 A

[56] References Cited

U.S. PATENT DOCUMENTS

| | | | |
|---|---|---|---|
| 1,589,670 | 6/1926 | Vartia | 602/19 |
| 1,924,016 | 8/1933 | Barrows | 602/19 |
| 2,117,309 | 5/1938 | Fritsch | 602/19 |
| 2,723,664 | 11/1955 | Davis | 602/19 |
| 3,570,480 | 3/1971 | Stubbs | 602/19 |
| 3,927,665 | 12/1975 | Wax | 602/19 |
| 4,135,503 | 1/1979 | Romano | 602/19 |
| 4,245,628 | 1/1981 | Eichler | 602/19 |
| 4,572,167 | 2/1986 | Brunswick | 602/19 |
| 4,964,401 | 10/1990 | Taigen | 602/19 |
| 5,086,759 | 2/1992 | Buddingh | 602/19 |

*Primary Examiner*—Michael A. Brown
*Attorney, Agent, or Firm*—John J. Posta, Jr.

[57] ABSTRACT

The back and stomach support device includes a) an elastic, flat, upraised, central back support, preferably tapering on its side margins from bottom to top, b) a first pair of flexible inelastic, elongated strips connected to the opposite sides of the central back support near the bottom thereof and sloping slightly upwardly as they extend laterally thereof; c) a second pair of such strips connected to the opposite sides of the central back support near the top thereof, overlapping the upper margins of the rear surfaces of the first pair of strips and sloping slightly downwardly as they extend laterally of the central back support; and, d) hook and loop fasteners on the strips. The strips wrap around the sides and front of the mid-section of a human torso for full support and overlap each other to an adjustable extent. The device can include a pair of elastic wings connected to the rear surface of the central back support and extending laterally behind the strips for releasable connection thereto to control the tension of the back support. The device can also include a removable pair of adjustable shoulder suspenders to hold the device in place when not in use.

10 Claims, 2 Drawing Sheets

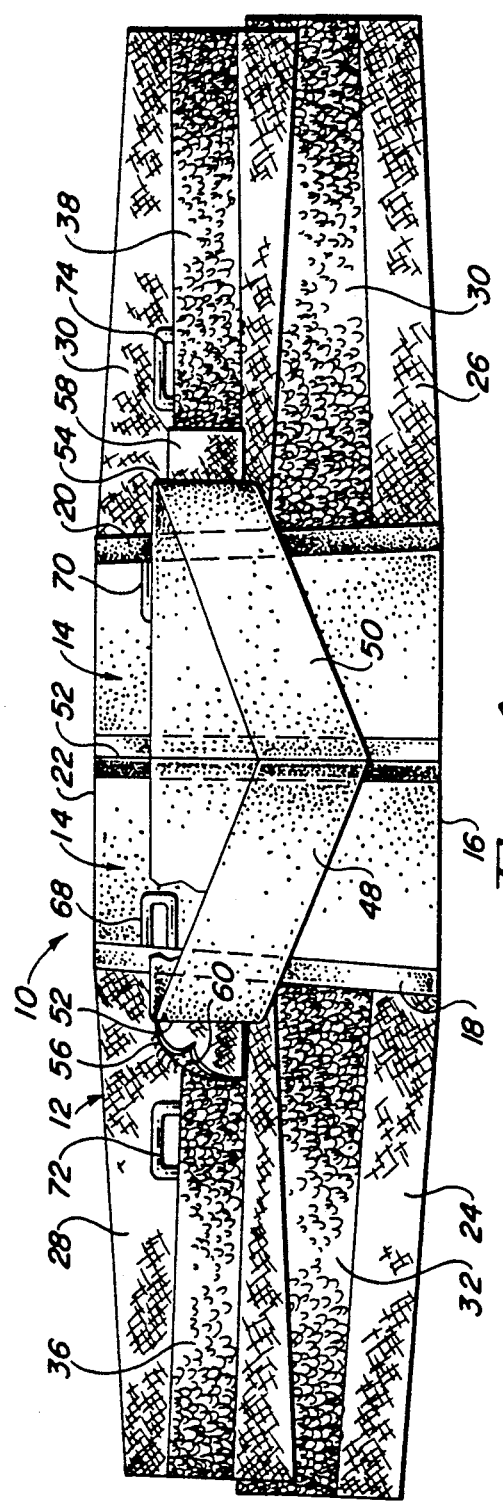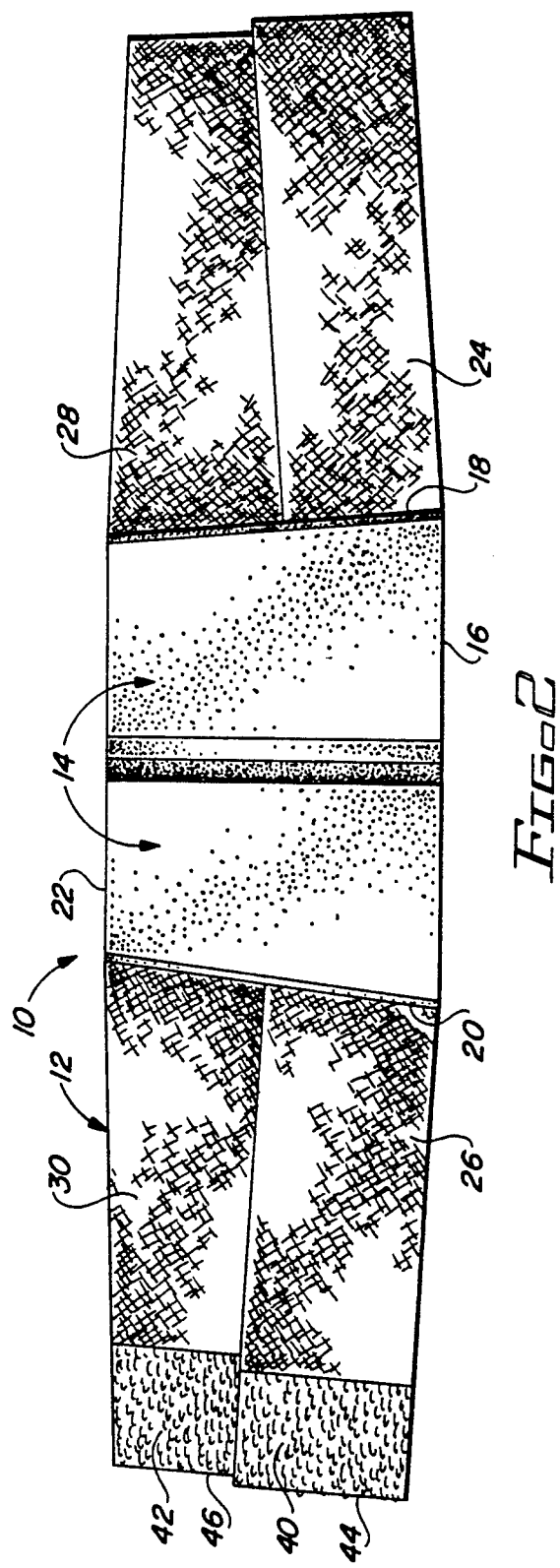

BACK AND STOMACH SUPPORT DEVICE

BACKGROUND OF THE INVENTION

1. FIELD OF THE INVENTION

The present invention generally relates to weightlifting protectors and more particularly to an improved back and stomach support device for weightlifters, stevedores and the like.

2. Prior Art

Various protective belts have been devised to help support the back and stomach of weightlifters, stevedores and the like in order to prevent strains and damage to muscles, soft internal organs, cartilage, and the spinal column and other bones during lifting of heavy weights such as are encountered by professional and amateur weightlifters, movers, stevedores, etc.

Thus, U.S. Pat. No. 4,964,401 discloses a belt with a rubber core in which is embedded an inflexible rigid strip. The core is backed by a strap of equal height, and the belt is releasably secured in front by overlapping opposed VELCRO parts. In one embodiment a buckle is provided to help cinch the belt. This belt has certain disadvantages: (1) the inflexible strip in the core makes close fitting of the belt to the body difficult and/or painful; and (2) since the core and backing strap are of the same height, they can dig in and pinch the skin during tightening of the belt.

There remains a need for an improved, inexpensive, durable weightlifting belt which will efficiently protect the weightlifter against muscle strain and prevent damage to the soft internal organs, cartilage and bones. The device should be easy to don and to center properly and should not pinch the skin, even when cinched tight. Preferably, the device can be left loosely in place without falling off. The device should also be capable of properly fitting around the mid-section of the female and male human torso, regardless of its particular anatomical shaft and size. Thus, the device should properly fit the body's natural contours. The device also should be designed to keep it from riding up on the body in use. The front portion of the device should provide efficient protection of the abdominal wall. It should also be designed to provide adjustable tension and compression for maximum comfort and protection.

SUMMARY OF THE INVENTION

The improved back and stomach support device of the present invention satisfies all the foregoing needs. The device is substantially as set forth in the Abstract of the Disclosure.

Thus, the device comprises the following components:
a) an elongated elastic, thin, flat, upraised cloth-type central back support, preferably slightly tapering at its side margins from bottom to top;
b) a first pair of flexible, inelastic, elongated strips connected to the opposite sides of the central back support near the bottom thereof, preferably sloping slightly upwardly as they extend laterally thereof;
c) a second pair of flexible, inelastic, elongated strips connected to the opposite sides of the central back support near the top of the latter, overlapping the upper margins of the rear surfaces of the first pair of strips of sloping slightly downwardly as they extend laterally of the central back support; and,
d) VELCRO fasteners on the strips so that they can overlap and be releasably fastened around the front of the waist of a user by such fasteners, for doubled abdominal support, and so that the pairs of strips can be adjustably releasably connected to each other for a correct anatomical fit.

The device can also include a pair of elastic wings connected to the side margins of the elastic central back support and extending laterally behind the strips for releasable VELCRO connection thereto, in order to adjust the back tension of the device. A pair of removable shoulder suspenders can also be provided, connected to the support device to hold the device in place when not in use.

Various other features of the invention are set forth in the following detailed description and accompanying drawings.

DRAWINGS

FIG. 1 is a schematic rear elevation of a preferred embodiment of the improved back and stomach support device of the present invention, the device being shown in the extended mode;

FIG. 2 is a schematic front elevation of the device of FIG. 1, the device being shown in the extended mode;

DETAILED DESCRIPTION

FIGS. 1-4

Figure 3:
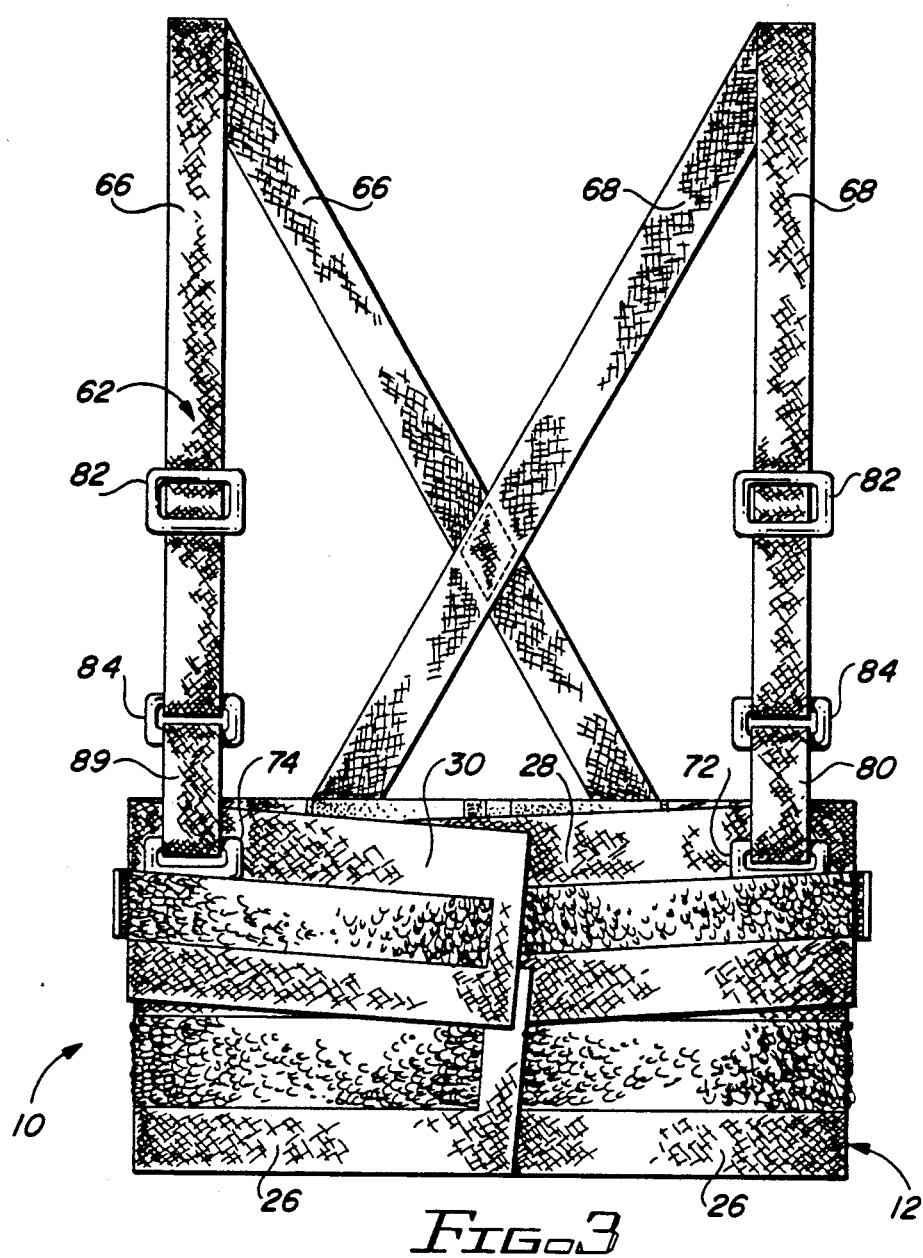
FIG. 3 is a schematic front elevation of the device of FIG. 1 shown with the pairs of strips overlapping in the front of the device, as when worne by a user, and with a pair of releasable shoulder suspenders in place on the device; and, FIG. 4 is an enlarged schematic fragmentary detail of the connection between a shoulder strap of the suspenders of FIG. 3 and the device of FIG. 3.
Figure 4:
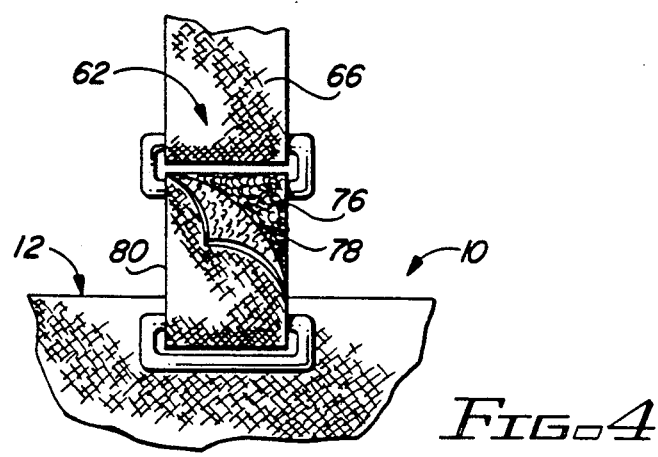

Now referring more particularly to FIGS. 1-4 of the drawings, a preferred embodiment of the improved back and stomach support device of the present invention is schematically depicted therein. Thus, device 10 is shown which comprises an elongated belt 12 comprising the following components:
a) The first component is an elongated, elastic, thin, flat upraised central back support 14 of elasticized cloth or elastomeric plastic or rubber, natural or synthetic, having a bottom 16, sides 18 and 20 and top 22, the latter preferably narrower than the bottom 16, so that sides 18 and 20 slope upwardly slightly towards each other.
b) The second component comprises a first pair of flexible, inelastic, elongated upraised strips 24 and 26, preferably of durable woven cloth, such as woven nylon or the like preferably padded connected to the opposite sides 18 and 20, respectively, of support 14 adjacent bottom 16 and extending laterally thereof for a distance sufficient to overlap each other (FIG. 3) when wrapped around the mid-section of a human torso. Strips 24 and 26 slope slightly upwardly as they extend laterally of support 14.
c) The third component comprises a second pair of flexible, inelastic, upraised, elongated strips 28 and 30 substantially identical to strips 24 and 26, but connected to the opposite sides 18 and 20 of support 14 adjacent top 22 and sloping slightly downwardly as they extend laterally of support 14. Strips 28 and 30 overlap the upper portions of the rear surfaces of strips 24 and 26. The two described pairs of strips 24, 26, 28 and 30 collectively provide lateral portions of belt 12 adapted to encircle the sides and front of the mid-section of a human torso, which belt portions progressively decrease in overall height from support 14 to the opposite ends of belt 12. This enables belt 12 to be form fitted to the torso, whether male or female. In this regard, strips 28 and 30 can overlap strips 24 and 26, respectively, a controlled variable degree, depending on the shape of the human torso.

d) The fourth component of the device comprises releasable securing means for device 10. These comprise the following:

1) There are elongated VELCRO receptor bands 32, 34, 36 and 38 connected to the rear surfaces (FIG. 1) of, respectively, strips 24, 26, 28 and 30, and mating VELCRO hook bands 40 and 42 connected to the front surfaces (FIG. 2) of the free ends 44 and 46 of, respectively, strips 26 and 30, as shown. Alternatively, such bands 40 and 42 could be on the free ends of strips 24 and 28. The VELCRO bands allow the pairs of strips to be releasably and adjustably held together, in overlapping relation to increase or decrease the heighth of belt 12 and to control its effective circumference around the waist of a user and also to control the tapering of belt 12 from back support 14 to its free ends.

2) There are also, optionally, a pair of elongated, flat, thin, narrow, elastic wings 48 and 50 of elasticized cloth or elastomeric plastic or rubber (FIG. 1), preferably connected to the rear surface of support 14 at about the center of the midline 52 thereof and extending preferably upwardly and laterally over the rear surfaces of, respectively, strips 28 and 30. The free ends 52 and 54 of, respectively, wings 48 and 50, are provided with laterally extending tabs 56 and 58, respectively, bearing on their front surfaces VELCRO hook areas 60 which releasably engage VELCRO receptor bands 36 and 38 to adjustably control the effective width of support 14 and thru the tension provided by back support 14.

e) A fifth optional component of device 10 comprises a pair of shoulder suspenders 62 comprising durable cloth shoulder straps 64 and 66 crossed in the rear. Straps 64 and 66 pass thru loops 68 and 70 connected to the rear surfaces of the upper portions of support 14 and through loops 72 and 74 connected to the mid-portions of the rear surfaces of strips 28 and 30 (FIGS. 1 and 3). Opposed VELCRO receptor surfaces 76 (FIG. 4) and VELCRO hook surfaces 78 on looped connector bands 80 trained around connector loops 84 on straps 64 and 66 releasably hold straps 64 and 66 to belt 12. Conventional strap shortening/lengthening buckles 82 are provided on straps 66 and 68.

Thus, an improved belt 12 is provided which, when worn about the waist, renders device 10 highly useful to hold the back, sides and front of the waist of a weightlifter in a secure, safe, strainless position and protects the muscles, bones and internal organs of the user against strain and damage. Device 10 can be shortened, lengthened, increased and decreased in back support and can be worne with or without suspenders. It is simple, easy to don, remove and use and is durable, inexpensive, attractive in appearance and capable of a wide variety of variations in sizes. It can be shaped to fit any torso.

Various modifications, changes, alterations and additions can be made in the improved support device of the present invention, its components and parameters. All such modifications, changes, alterations and additions as are within the scope of the appended claims form part of the present invention.

What is claimed is:

1. An improved back and stomach support device, said device comprising, in combination:
   a) a generally flat, upraised, central, elastic, flexible, and stretchable back support with a top, bottom, and sides;
   b) a first pair of generally flat, flexible, upraised, inelastic, elongated strips connected to said opposite sides said central back support adjacent said bottom of said support and extending laterally thereof and adapted to be wrapped around the sides and front of the mid-section of a human torso;
   c) a second pair of generally flat, upraised, flexible, inelastic elongated padded strips connected to said opposite sides of said central back support adjacent said top of said support and extending laterally thereof, overlapping the rear surface of the upper portion of said first pair of strips and adapted to be wrapped around the sides and front of the mid-section of a human torso; and,
   d) adjustable securing means on said strips to releasably hold said strips in an overlapped back and front support position on the mid-section of a human torso.

2. The improved support device of claim 1 wherein said first pair of strips are sloped upwardly and said second pair of strips are sloped downwardly to provide a belt which gradually decreases in height from said back support to conform to a human mid-section and to provide efficient overlapping of said pairs of strips.

3. The improved support device of claim 2 wherein said securing means comprises hook and loop fasteners on said strips.

4. The improved support device of claim 3 wherein said fasteners are on adjoining surfaces of said strips along the length thereof.

5. The improved support device of claim 1 wherein said central back support comprises elasticized cloth and wherein said first and second pairs of strips comprise padded cloth.

6. The improved support device of claim 1 wherein said device includes a pair of flexible, resilient wings, one end of which is secured to the rear surface of said central support adjacent the center thereof, said wings extending laterally outwardly thereof over the rear surface of one of said pairs of strips, and wherein said wings bear means for releasably securing said wings to said rear surfaces of said strips for adjusting the effective stretchability strength and length of said central back support.

7. The improved support device of claim 6 wherein said wing securing means comprise hook and loop fasteners on said wings and said rear surfaces of said strips.

8. The improved support device of claim 1 wherein said central back support and said second pair of strips bear loop fasteners, and wherein said device includes removable, adjustable shoulder suspenders releasably connected to said device through said loop fasteners.

9. The improved support device of claim 1 wherein said central support is wider at the bottom thereof than the top thereof, gradually tapering therebetween for a contoured waist fit.

10. The improved support device of claim 1 wherein said central back support comprises elasticized cloth and wherein said cloth strips comprise nylon.

* * * * *